(12) United States Patent
Nakamura (10) Patent No.: US 8,074,364 B2
(45) Date of Patent: Dec. 13, 2011

(54) HOLDER FOR A SURGICAL KNIFE BLADE

(75) Inventor: Shoichi Nakamura, Nagano (JP)

(73) Assignees: ACP Japan Co., Ltd., Tokyo (JP);
Shoichi Nakamura, Nagano (JP)

( * ) Notice: Subject to any disclaimer, the term of this patent is extended or adjusted under 35 U.S.C. 154(b) by 681 days.

(21) Appl. No.: 12/085,661

(22) PCT Filed: May 17, 2006

(86) PCT No.: PCT/JP2006/309782
§ 371 (c)(1),
(2), (4) Date: Jun. 27, 2008

(87) PCT Pub. No.: WO2007/069352
PCT Pub. Date: Jun. 21, 2007

(65) Prior Publication Data
US 2009/0165310 A1 Jul. 2, 2009

(30) Foreign Application Priority Data
Dec. 15, 2005 (JP) .................. 2005-362472

(51) Int. Cl.
*B26B 1/08* (2006.01)
*A61B 17/32* (2006.01)
(52) U.S. Cl. ............... 30/335; 30/162; 606/167
(58) Field of Classification Search .............. 30/162, 30/335, 337, 339; 606/167
See application file for complete search history.

(56) References Cited

U.S. PATENT DOCUMENTS

| 4,617,738 | A | | 10/1986 | Kopacz | |
|---|---|---|---|---|---|
| 5,431,672 | A | | 7/1995 | Cote et al. | |
| 5,571,127 | A | * | 11/1996 | DeCampli | 606/167 |
| 5,938,676 | A | * | 8/1999 | Cohn et al. | 606/167 |
| 6,022,364 | A | * | 2/2000 | Flumene et al. | 606/166 |
| 6,254,621 | B1 | * | 7/2001 | Shackelford et al. | 606/167 |
| 6,949,109 | B2 | * | 9/2005 | Iske et al. | 606/167 |
| 7,101,382 | B2 | * | 9/2006 | George et al. | 606/167 |
| 2004/0098001 | A1 | * | 5/2004 | Holman | 606/167 |
| 2005/0065541 | A1 | * | 3/2005 | Abidin et al. | 606/167 |

FOREIGN PATENT DOCUMENTS

| JP | H02-060641 | | 3/1990 |
|---|---|---|---|
| JP | 2003-339723 | | 12/2003 |
| JP | 2007-159939 | * | 6/2007 |
| WO | WO 01/05312 | | 1/2001 |

* cited by examiner

*Primary Examiner* — Hwei C Payer
(74) *Attorney, Agent, or Firm* — Manabu Kanesaka (57) ABSTRACT

A holder for a surgical knife blade has a holder body, a slide member supported slidably by the blade storage barrel, an attaching finger formed in part of the slide member to attach the surgical knife blade, a slide operating piece integrally formed with the slide member, a lock hook member that prevents the slide member from sliding, locking concave grooves disposed in a slide guide edge of the holder body which guides the slide member slidably and engaging in the lock hook member, and a lever device, coupled to the slide member, for supporting the lock hook member while biasing the lock hook member toward the locking concave groove. The locking concave grooves are formed in an attachment position where the surgical knife blade is attached to the attaching finger in the slide member. In a storage position, the surgical knife blade is stored in the storage barrel.

4 Claims, 10 Drawing Sheets

X-X CROSS-SECTIONAL VIEW

HOLDER FOR A SURGICAL KNIFE BLADE

TECHNICAL FIELD

The present invention relates to a surgical knife blade holder which accommodates a surgical knife for surgical operations, and which is a holder for surgical operations enabling a surgical knife blade stored in a storage case to be attached to a holder body with a single motion.

BACKGROUND ART

Conventionally, as a surgical knife used in surgical operations, there have been known two types that a handle portion to be grasped when used and a blade edge portion at the front end of the handle portion are formed integrally, and that a knife blade and a holder are formed separately while the knife blade is attached to the front end of the handle when used. The latter type of knife such that the handle and knife blade are manufactured and supplied separately and incorporated when used is widely used. When such a knife is a knife for work, the knife blade is exchanged with a new knife blade according to the wearing state of the blade edge. Meanwhile, when such a knife is a surgical knife, the knife is used as disposal equipment while a used knife blade is discarded and exchanged with a new knife blade. Conventionally, in the case where a knife blade is attached to an attachment portion such as a slit or the like provided at the front end portion of the holder body grasped when used, a user holds a knife blade with one hand and fingers to attach, while holding the attachment portion of the holder body to fix using the other hand and fingers or using a device such as a forceps or the like.

However, since the surgical knife is formed particularly acutely, there is a risk of injury such as hurt and the like when the surgical knife is attached or detached, and it is required to attach and detach the surgical knife safely and easily. Therefore, in the case of the surgical knife, for example, Patent Document 1 proposes a structure where a case-shaped guard is provided in a surgical knife blade, and fitted and attached to a handle, and the internal knife blade is caused to protrude outside the guard with an operational slider provided on the handle side when the surgical knife blade is used after being attached. Accordingly, the guard with the internal knife blade is attached and fixed to the handle to be used, and the knife blade is removed from the handle together with the guard and discarded after being used. The publication describes sterilizing the guard to distribute, and thereby preventing infection when the guard is attached to the handle and used.
Patent Document 1: JP 2003-504145

DISCLOSURE OF INVENTION

Problems to be Solved by the Invention

As described above, when a surgical knife blade is attached as an attachment to a holder in accordance with the intended use or detached to be discarded, it is danger for a user to directly hold the surgical knife blade using fingers and the like to attach or detach, and it is pointed out also in Patent Document 1 that exchanging an acute blade such as a surgical knife or the like in emergency results in a risk of unintentional damage. Therefore, Patent Document 1 discloses the method and structure where an attachment (guard) with an internal surgical knife blade is attached to a holder detachably. Such a type that the attachment with the internal surgical knife blade is attached and detached is expensive because the guard is exchanged, and has problems that the attachment rattles when attached to the holder and that the operation for loading or unloading the surgical knife blade is not performed smoothly unless the attachment is manufactured precisely. Further, it is not possible to adapt such an attachment to holders to attach using fingers which are already commercially available and used. Furthermore, when bacteria adhere to the surgical knife blade or the holder protecting the blade in a medical operation and the like, there is a risk of infection, and the problem arises that the holder with the internal surgical knife blade needs sterilization packing to be distributed.

The method of Patent Document 1 according to the conventional technique has defects that the manufacturing cost is high and that the distribution cost is also high because consideration must be given to distribution to prevent bacteria from adhering and the attachment from being deformed by impact and the like. Therefore, it is an object of the invention to provide a holder for a surgical knife blade enabling only the surgical knife blade stored in a case to be attached to the holder without coming into contact with the surgical knife blade, providing easy and safe attachment to the holder, and further enabling bacteria and the like to be prevented from adhering.

Means for Solving the Problem

In view of the above-mentioned problems, the present invention provides a holder for a surgical knife blade characterized by comprising a holder body that has a blade storage barrel and that is formed in an appropriate shape to grasp, a slide member that is supported slidably by the blade storage barrel, an attaching finger that is formed in part of the slide member to attach a surgical knife blade, a slide operating piece that is integrally formed with the slide member, a lock hook member that prevents the slide member from sliding, locking concave grooves that are disposed in a slide guide edge of the holder body which guides the slide member slidably and that engage in the lock hook member, and lever means, coupled to the slide member, for supporting the lock hook member while biasing the lock hook member toward the locking concave groove side, where the locking concave grooves are formed in an attachment position where the surgical knife blade is attached to the attaching finger in the slide member, in a use position where the attached blade is fixed, and in a storage position where the surgical knife blade is stored in the storage barrel. By this means, the surgical knife holder according to the invention achieves extremely easy attachment of a surgical knife blade without coming into contact with the surgical knife blade with the surgical knife blade stored in a case.

Herein, the attaching finger is provided with an engagement portion adapting to a fit hole formed in the surgical knife blade, and in the edge of the engagement portion is formed a wing to support a drop of the surgical knife blade when the surgical knife blade is fitted. By this means, the surgical knife blade fitted into the attaching finger of the holder does not remove.

Further, the attaching finger is characterized in that in its upper plane is formed an engagement portion which is fitted into the surgical knife blade, and that in its rear bottom is formed an insertion guide which adapts to an insertion guide of a storage case storing the surgical knife blade and guides insertion of the attaching finger. Herein, the insertion guide adapts to a protrusion or a concave-shaped groove that is the insertion guide of the storage case, and is a concave-shaped groove or a protrusion, respectively. By this means, the attaching finger is smoothly inserted into the storage case, while it is made easy that the surgical knife blade is fitted into the attaching finger.

Furthermore, the slide member is provided with a wing member, at the back of the attaching finger corresponding to the attachment position where the surgical knife blade is attached to the attaching finger in the slide member, to separate an upper case and a lower case forming the storage case. Then, the wing member is formed so that a thickness at its front end portion is thinner than a thickness at its rear end portion. By this means, only by inserting the attaching finger, it is possible to easily separate the upper case and the lower case forming the storage case.

Advantageous Effect of the Invention

Thus, in the holder for a surgical knife blade according to the invention, the slide member provided with the attaching finger is provided slidably in the blade storage barrel of the holder body, the slide operating piece for operating the slide member to slide is engaged and locked in the attachment position, use position and storage position in this order from the front end to the rear end side of the holder body by the lock hook member, the attaching finger is thereby locked in the attachment position reliably when the surgical knife blade is attached, and an operator grasps the holder body with one hand and fingers, while grasping the storage case with the other hand and fingers, and in this state, is capable of attaching the internal surgical knife blade by inserting the attaching finger of the holder body into the insertion guide hole of the storage case. Further, since the slide member provided with the attaching finger is engaged and locked in the attachment position, use position and storage position in this order after the attachment, it is made possible to operate the surgical knife blade with easy operation from attachment to a usage state, and further to a storage state after being used.

Then, the blade is attached to the holder body by inserting the attaching finger fixed into the attachment position of the holder body along the insertion guide hole formed in the storage case, and by pulling it, the surgical knife blade can be taken out of the storage case while being attached, whereby it is possible to attach the blade with a single motion. Accordingly, when attaching, the operator does not touch the surgical knife blade, is thereby safe, and does not have the risk of injury. Further, the risk is eliminated that bacteria and the like adhere to the surgical knife blade and result in infection.

BRIEF DESCRIPTION OF DRAWINGS

FIG.1 contains perspective views showing appearances of a holder and a blade storage case used together with a holder handle according to the invention, where FIG.1(*a*) shows the holder, and FIG.1(*b*) shows the storage case;

FIG.2 shows the structure of the holder of FIG.1, where FIG.2(*a*) shows the holder body, FIG.2(*b*) shows the rear bottom of a slide member, and FIG.2(*c*) shows the upper plane of the slide member;

FIG.3 shows states where a surgical knife blade is attached to the holder of FIG.1, where FIG.3(*a*) shows a state where the surgical knife blade is attached to an attaching portion, FIG.3(*b*) shows a state where the attached knife blade is fixed in a use position, and FIG.3(*c*) shows a state where the knife blade is stored in the holder;

FIG.4 contains explanatory views of the knife blade being attached to the attaching portion (attaching finger) of the holder of FIG.1, where FIG.4(*a*) is a perspective view of the attachment state, and FIG.4(*b*) shows an X-X cross-sectional view of FIG.4(*a*);

FIG. 5(*a*) is an exploded perspective view showing the blade storage case of FIG. 1, and FIG. 5(*b*) shows an explanatory view illustrating a structure of the storage case;

FIG. 6 shows procedures to attach the knife blade in the storage case to the holder as shown in FIG. 1, where FIG. 6(*a*) is a state view where the holder is attached, FIG. 6(*b*) is a state view of an initial state of the holder being inserted in the storage case, FIG. 6(*c*) shows a state view immediately before the blade in the storage case and the attaching portion of the holder are engaged, FIG. 6(*d*) shows a cross-sectional view taken along linex-x in FIG. 6(*b*), and FIG. 6(*e*) shows a cross-sectional view taken along line x-x in FIG. 6(*c*);

FIG. 7 shows the same procedures as in FIG. 6, where FIG. 7(*d*) is a state view where the blade in the storage case is attached to the attaching portion of the holder, FIG. 7(*e*) is a state view where the holder is pulled out of the storage case after the attachment, FIG. 7(*f*) is a state view where the knife blade is fixed to a use position of the holder, FIG. 7(*g*) is a state view where the knife blade is stored in a storage barrel, FIG. 7(*h*) shows a cross-sectional view taken along line x-x in FIG. 7(*d*), and FIG. 7(*i*) shows a cross-sectional view taken along line x-x in FIG. 7(*e*)

BEST MODE FOR CARRYING OUT THE INVENTION

Figure 1A:
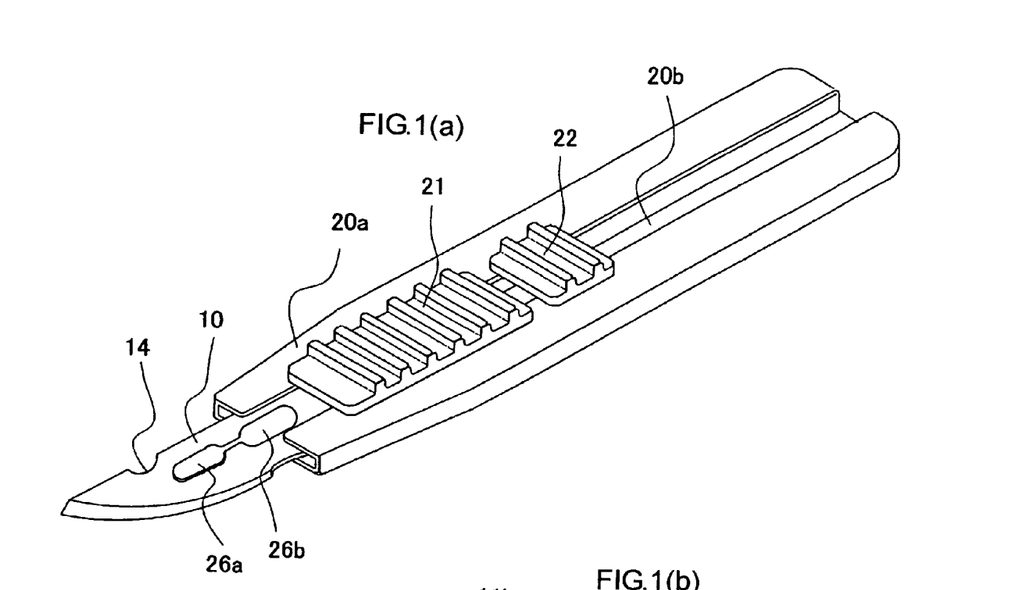
Figure 1B:
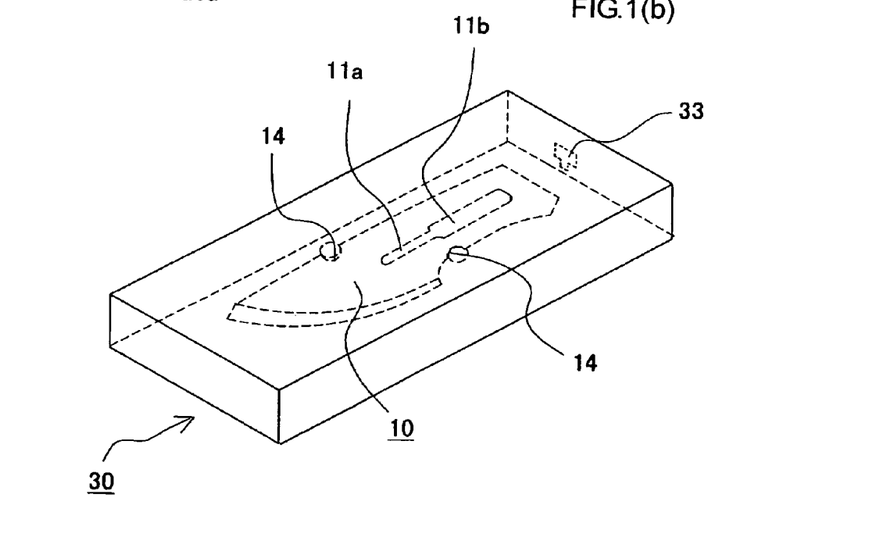
Figure 2A:
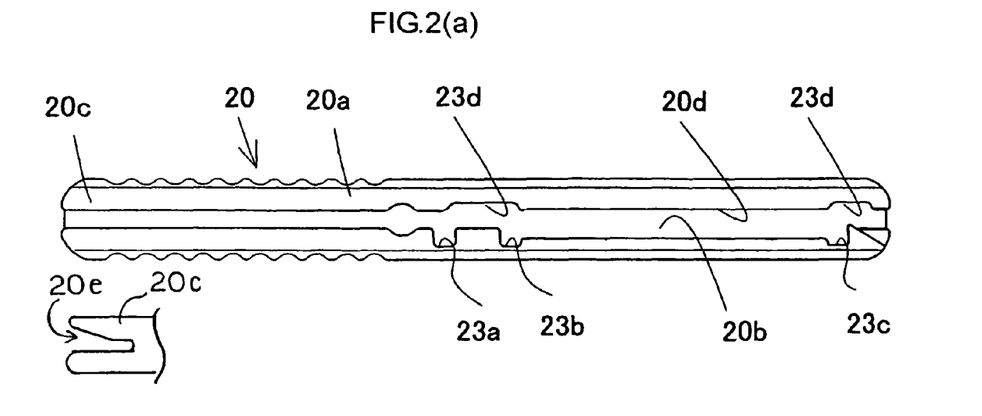
Figures 4A, 4B:
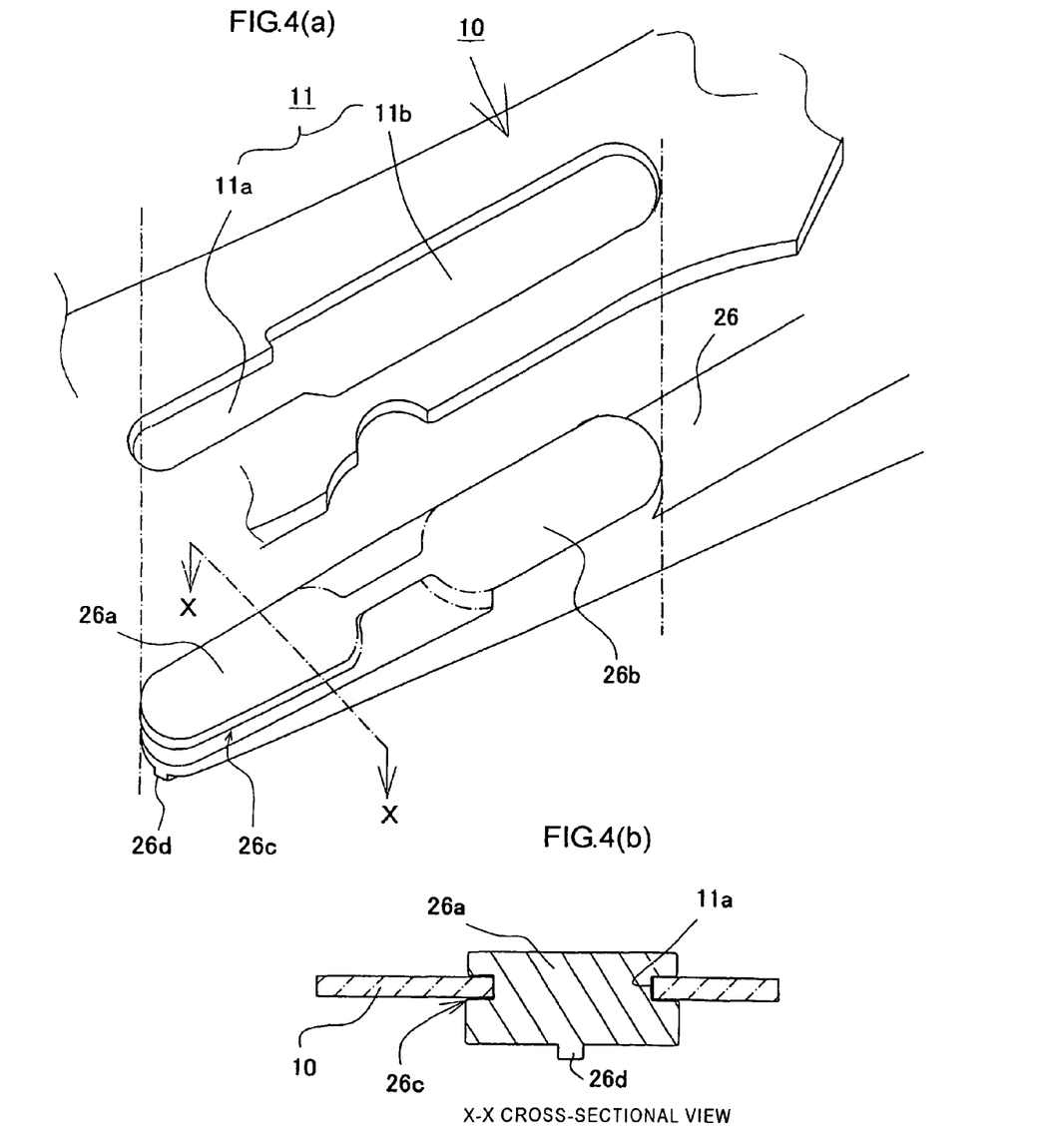
Figure 5A:
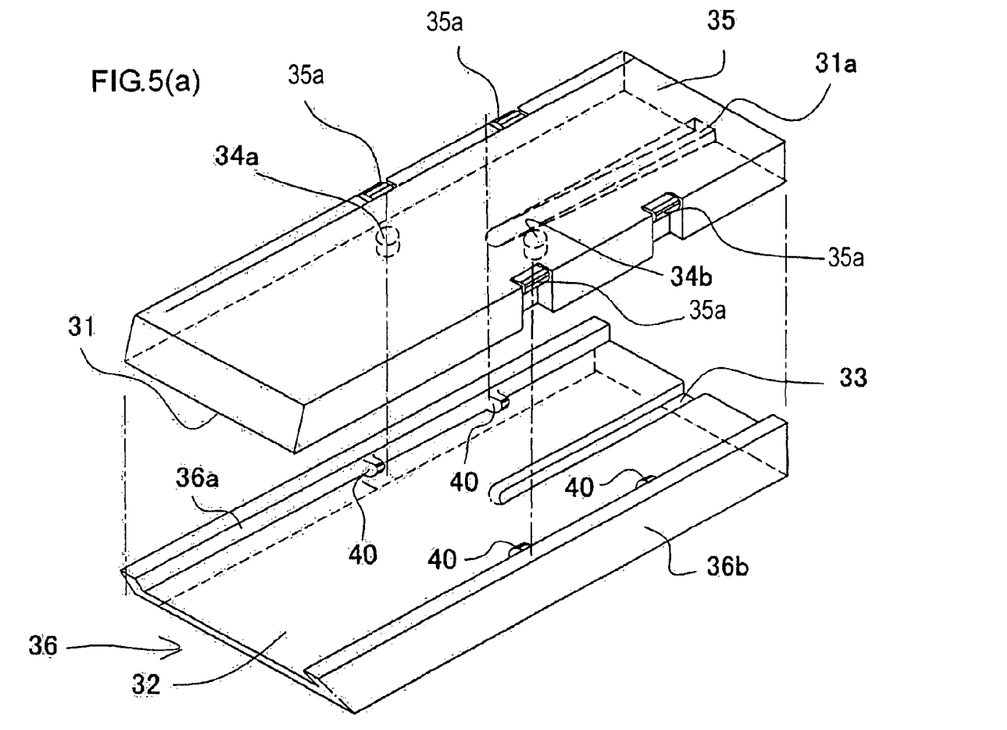
Figure 5B:
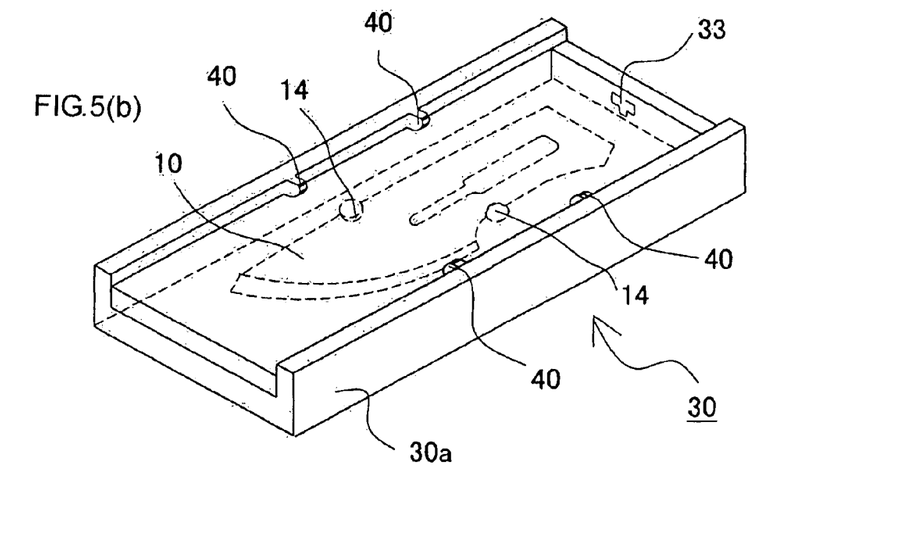

The present invention will specifically be described below based on preferred embodiments shown in accompanying drawings. FIG. 1 contains perspective views showing appearances of a holder and a storage case with an internal surgical knife blade when the invention is applied to a surgical knife. FIGS. 2, 3 and 4 are explanatory views illustrating an attachment engagement mechanism of the holder and surgical knife blade. FIG. 5 contains explanatory views illustrating a structure of the storage case.

Described first is the structure of the holder of the invention. As shown in FIG. 1, a typical holder widely used for a surgical knife is comprised of a holder body 20*a*, and an attaching finger 26 in the shape of a bar formed to protrude from the front end of the body. As shown in FIG. 3, the finger 26 is formed to be rectangle in cross section and in the shape of a bar with an appropriate length, and is provided with an engagement portion in the shape adapting to a fit hole 11 of the surgical knife blade described later at two portions, first engagement portion 26*a* and second engagement portion 26*b*. In the first engagement portion 26*a*, as shown in FIG. 4(*b*), a slit concave portion 26*c* is formed on its side face.

Meanwhile, the surgical knife blade 10 is formed to have a shape of a blade edge in accordance with the intended use, and provided at its base portion with the fit hole 11 adapting to the engagement portion of the finger 26 at two portions, first fit hole 11*a* and second fit hole 11*b*. Then, the first fit hole 11*a* is formed in the shape of engaging in the first engagement portion 26*a*, while the second fit hole 11*b* is formed in the shape of engaging in the second engagement portion 26*b*. Further, in order for an edge portion of the first fit hole 11*a* formed in the surgical knife blade to mesh with the slit concave portion 26*c* formed on the side face of the first engagement portion 26*a*, the groove thickness of the slit concave portion 26*c* is configured to be the shape substantially in accordance with the thickness of the surgical knife blade. Thus, the attaching finger 26 is provided with the engagement portion 26 adapting to the fit holes 11a and 11b formed in the surgical knife blade 10, and in the edge of the engagement portion 26 is formed the slit concave portion 26c to support a drop of the surgical knife blade 10 more than necessary when the surgical knife blade is fitted.

The surgical knife blade 10 thus attached to the attaching finger 26 is regulated in a fit in the horizontal direction by the first and second engagement portions 26a and 26b, while being regulated in a fit in the vertical direction by the slit concave portion 26c, and integrally attached to the attaching finger. Further, in the holder as shown in the figure, as described later, the attaching finger 26 is fitted and supported slidably in a storage barrel 20b formed in the holder body 20a, and the finger 26 is integrally provided with a slide operating piece 21a and lock operating piece 22. Then, in the storage barrel 20b, engagement lock grooves 23 to fix the attaching finger 26 are provided in a plurality of portions, and when a lock hook member 24 provided on the lock operating piece 22 side is engaged in the lock groove 23, the attaching finger 26 is fixed in this position.

Figure 2B:
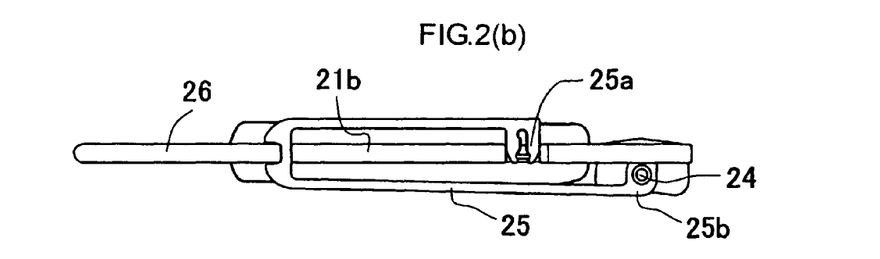
Figure 2C:
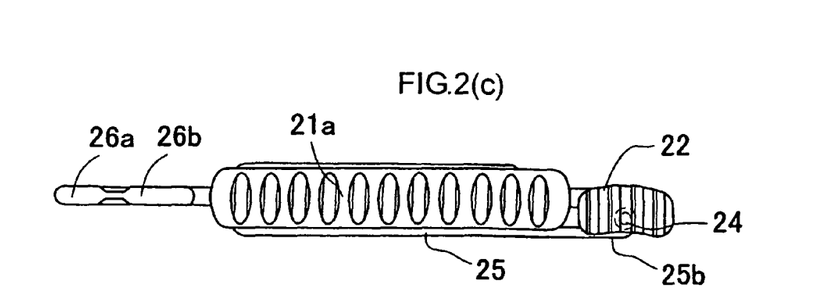

Further, when the lock operating piece 22 is moved in the direction of the arrow in FIG. 2 against a biasing spring (not shown), the lock is released, and the attaching finger is movable using the slide operating piece 21a. The attaching finger 26 is locked in three portions, (a) surgical knife blade attachment/detachment position, (b) usage state, and (c) storage state, and particularly, in the usage state, concurrently with the surgical knife blade 10 being engaged in the engagement portion of the attaching finger 26 as described previously, the base portion of the surgical knife blade is fitted into the fixing portion 23a formed in the storage barrel 20b of the holder body and is reliably fixed to the holder. Further, as shown in FIG. 3(c), the surgical knife blade 10 can be stored in the storage barrel 20b of the holder body 20a.

The structure of the holder body will specifically be described below based on FIG. 2. The holder body 20a as described above is formed in the appropriate shape easy to grasp corresponding to the purpose of use, and for example, formed by synthetic resin mold forming or aluminium diecast forming. The holder body 20a is provided with the storage barrel 20b, and is formed in the shape of a sheath to store the surgical knife blade 10 inside thereof. Further, the holder body 20a is provided with a slit-shaped guide groove 20d in the longitudinal direction. The slide member 21 as shown in FIG. 2(b) is fitted and stored in the guide groove 20d in the longitudinal direction. FIG. 2(b) shows the back of the slide member 21, and FIG. 2(c) shows the front of the slide member 21. The slide member 21 is integrally provided at its back side with a protrusion thread rail 21b adapting to the guide groove 20d, while being integrally provided at its front side with the slide operating piece 21a. Further, in a front end portion 20c of the holder body 20a, a groove-shaped surgical knife blade accepting portion 20e is formed to accept a rear end portion (end portion opposite to the blade edge) of the surgical knife blade 10 in mounting the surgical knife blade (see FIG. 1) to the holder 20. By this means, when the surgical knife blade 10 is pulled from the attachment position as shown in FIG. 3(a) to the usage state as shown in FIG. 3(b) in the holder 20, the surgical knife blade 10 is prevented from dropping from the attaching finger 26 with the blade edge pointed downward.

Then, the rail 21b is fitted into the guide groove 20d, and supported slidably in the longitudinal direction of the holder body 20a by the slide operating piece 21a. In the slide member 21, a hook biasing member 25 is fixed at its one end 25a from a spring piece in the shape as shown in the figure, while being fixed at the other end 25b to a lock hook member 24. The lock hook member 24 is fixed to the hook biasing member 25 integrally with the lock operating piece 22, and the member 24 shown in the figure is comprised of a pin member. Then, the hook biasing member 25 biases the lock hook member 24 in the direction of the arrow shown in the figure.

Meanwhile, in the holder body 20a, the guide groove 20d is provided with an engagement lock groove 23 that engages in the lock hook member 24. The engagement lock groove 23 fixes the slide member 21 fitted into the guide groove 20d in a predetermined position. In other words, the lock hook member 24 installed in the slide member 21 is fitted into the engagement lock groove 23 by a spring force of the hook biasing member 25 so as to fix the slide member 21 into this position. The lock operating piece 22 is formed integrally with the lock hook member 24, releases the engagement with the engagement lock groove 23 against the spring force of the hook biasing member 25, and enables the slide member 21 to slide. In addition, "23d" shown in the figure is an escape groove for the lock operating piece 22 and formed in the guide groove 20d.

Figure 3A:
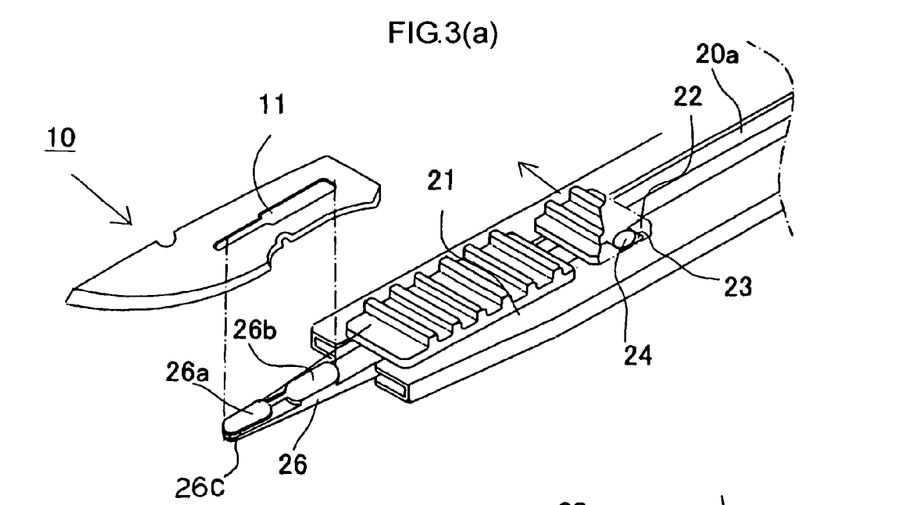
Figures 3B, 3C:
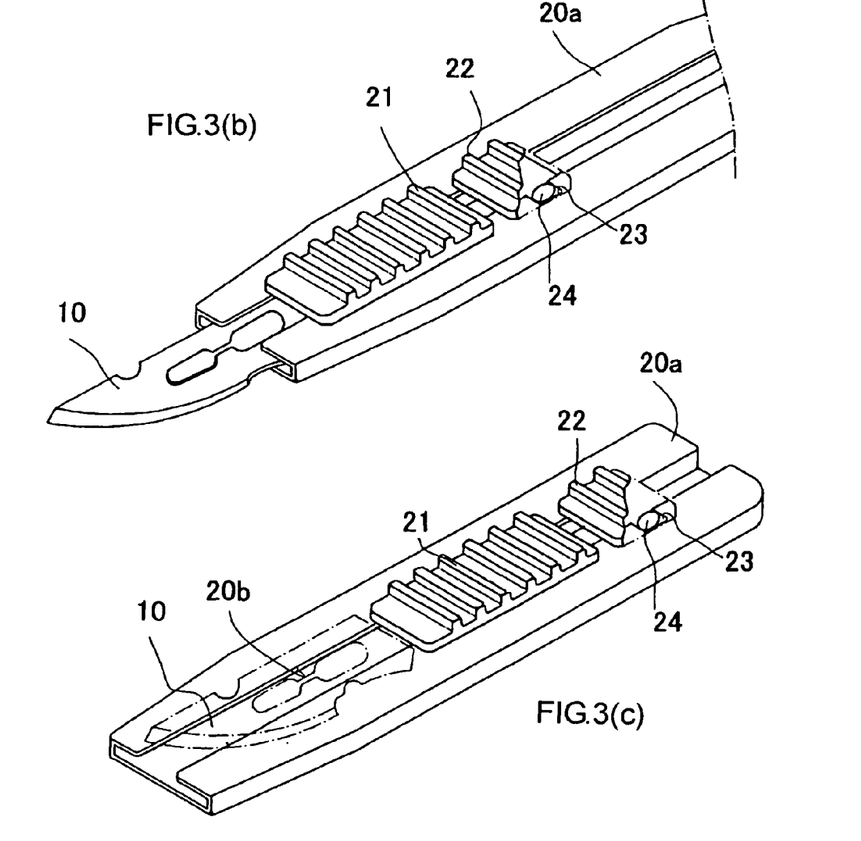

In the engagement lock groove 23 are arranged a first lock groove 23a to fix the slide member 21 to the attachment position as shown in FIG. 3(a), the second lock groove 23b to fix the member 21 to the use position, and a third lock groove 23c to fix the member 21 to the storage position in this order from the front end to the rear end side of the holder body 20a. Then, when the slide member 21 is in the attachment position as shown in FIG. 3(a), the attaching finger 26 formed at the front end of the member 21 protrudes outside from the storage barrel 20b. Further, in the use position as shown in FIG. 3(b), a base portion 10a of the surgical knife blade 10 attached to the attaching finger 26 is supported by the storage barrel 20b. Then, in the storage position as shown in FIG. 3(c), the surgical knife blade 10 is completely stored inside the storage barrel 20b. For movement of the slide member 21, the lock operating piece 22 is moved by finger in the direction opposite to the direction of the arrow shown in FIG. 3 to remove the lock hook member from each of the first, second and third lock grooves, and in this state, the slide member 21 is slightly moved.

The invention aims to enable the surgical knife blade 10 to be attached to the attaching finger 26 of the holder with the surgical knife blade 10 stored in the storage case 30 in attaching the surgical knife blade 10 to the holder 20 with the above-mentioned configuration. The storage case 30 will be described below. As shown in FIG. 5, the storage case 30 is formed in the shape of a box capable of storing the surgical knife blade 10 corresponding to the shape of the surgical knife blade 10. The storage case 30 is comprised of a box-shaped case body 30a forming a housing, an upper support face 31 and lower support face 32 that support the surgical knife blade inside the case body, an insertion guide hole 33 formed in one of the upper and lower support faces, and a blade fixing piece 34 that fixes the surgical knife blade. In the case as shown in FIG. 5, the case body is comprised of an upper case 35 and a lower case 36, and the inner surface of the upper case 35 is the upper support face 31, while the inner surface of the lower case 36 is the lower support face 32. Then, the upper case 35 is detachably connected in the shape of a lid and thus coupled to the lower case 36 to be able to separate (the structure will be described below.)

Then, the lower support face 32 is provided with the insertion guide hole 33 that guides the attaching finger 26 along the lower face of the surgical knife blade from the outside of the case. This is because of inserting the attaching finger 26 of the holder 20 in the plate-shaped blade 10 stored in the case body 30a to engage the finger 26 and the blade 10 with each other, and attaching the surgical knife blade to the holder. Accordingly, the insertion guide hole 33 is formed in the shape adapting to the attaching finger 26, and it is formed that the insertion of the finger engages the fit holes (the first fit hole 11a and second fit hole 11b described previously) of the surgical knife blade mounted and supported on the lower support face and the first and second engagement portions 26a and 26b of the finger 26 with each other, respectively. In particular, in the case as shown in the figure, to facilitate the insertion of the finger, a guide 26d formed of a protrusion or concave portion is formed in the bottom in the longitudinal direction on the back side of the finger 26 having the engagement portions 26 on its upper face, while a guide rail 33a is formed in the insertion guide hole 33 to be fitted with the guide 26d.

Figure 6A:
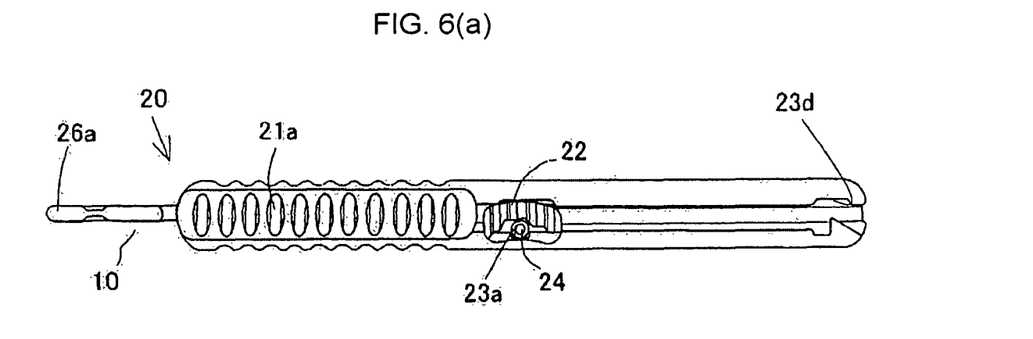
Figure 6B:
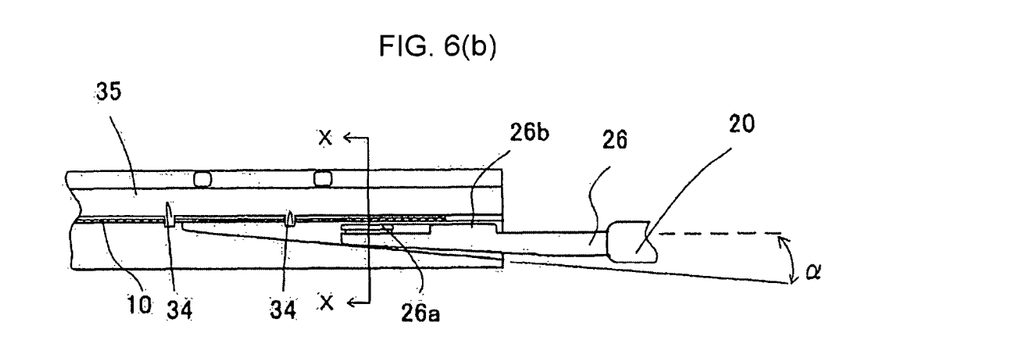

By this guide rail, without exactly matching the cross-sectional shape of the insertion guide hole 33 and the cross-sectional shape of the finger, the finger is guided along the guide rail, and the insertion guide hole can thereby be manufactured readily. Further, in the insertion guide hole 33, as shown in FIG. 6, the bottom is inclined an angle of α as shown in FIG. 6(b) so that the first and second engagement portions are brought closer to the upper support face 31 side with the entry of the attaching finger. This is because the engagement portions 26a and 26b of the attaching finger slip into the fit holes 11 of the surgical knife blade 10 mounted on the lower support face 32 from the insertion guide hole 33 formed in the lower support face i.e. from the state of FIG. 6(b) to the state of FIG. 6(c). The insertion guide hole 33 is thus inclined. Alternately, the lower support face may be inclined to store the tilting surgical knife blade, and in this case, the lower support face is inclined an angle of −α in the opposite direction.

Further, instead of forming such an incline, space may be formed between the upper and lower support faces so that the surgical knife blade rises from the lower support face by the entry of the finger. In the case as shown in the figure, the insertion guide hole 33 is inclined an angle of α as shown in the figure, while a small gap is formed between the upper and lower support faces to raise the surgical knife blade slightly from the lower support face. This is because the edge portion of the first fit hole 11a of the surgical knife blade is caused to mesh with the slit concave portion 26c of the first engagement portion 26a of the attaching finger in the state of FIG. 7(d).

Described herein is the coupling structure of the upper case 35 and lower case 36 as described above. As shown in FIG. 5, the lower case 36 is comprised of integrally formed left and right side walls 36a and 36b, lower support face 32 and insertion guide hole 33 by synthetic resin mold forming. Further, the upper case 35 is also formed of a plate-shaped synthetic resin, the upper support face 31 is formed in the inner bottom, and the concave groove 31a is ditched in the face 31. The concave groove 31a is an escape groove to avoid causing the engagement portions 26 of the finger to interfere in pulling the attaching finger 26 inserted from the insertion guide hole 33 (formed in the lower case) as described previously out of the case with the surgical knife blade attached to the finger. The upper case 35 and lower case 36 forming the storage case are formed of a material capable of causing elastic deformation such as a synthetic resin or the like, and preferably, include an X-ray impermeable additive such as barium sulfate and the like.

Further, the upper support face 31 is provided with a blade fixing piece 34 formed of protrusions 34a and 34a obtained by planting pins. The protrusions 34a and 34b are arranged in positions that engage the protrusions in engagement concave recess portions 14 formed in the surgical knife blade 10. This is because of preventing the surgical knife blade from being pushed and moved in inserting the attaching finger from the insertion guide hole 33, and also preventing the stored surgical knife blade from rattling in the transport process. In the blade fixing piece 34 shown in the figure, in order not to cause damage to the cutting function of the surgical knife blade 10, the protrusions 34a and 34b are arranged in positions to engage in the portions 14 each formed of a notch on the surgical knife blade side respectively in the back of the blade and in the base portion on the blade surface side. In the example as shown in FIG.5a, the protrusions 34a and 34b are provided on the upper support face 31 side of the upper case 35, while the engagement concave recess portions 14 are provided on the blade 10. Alternately, the concave recess portions 14 may be provided on the upper support face 31 side of the upper case 35, while the protrusions 34a and 34b may be provided on the blade 10.

Thus formed upper case 35 is fitted into between the left and right side walls 36a and 36b of the lower case 36 in the shape of a lid, and the left and right side walls 36a and 36b are provided with locking protrusions 40. The locking protrusions 40 are provided in a few portions as appropriate in the left and right side edges 36a and 36b so as to hold the upper case in a position that the surgical knife blade 10 mounted on the lower support face 32 is held vertically between the upper support face 31 and face 32, and engage in the locking edge 35a of the upper case. In particular, the locking protrusion 40 as shown in the figure are formed to cause elastic deformation in the side walls of the lower case formed of a synthetic resin with elasticity, and thereby cause snapping operation in inserting the attaching finger 26 as shown in FIG. 6(b). In other words, when the upper case 35 is pushed upward from below, the locking edge 35a climbs over the locking protrusions 40 and separates from the lower case, and at this point, the protrusions 40 perform the snapping operation. In addition, the snapping operation can be adjusted by forming thin portions that tend to cause elastic deformation in the left and right side edges 36a and 36b, forming a slit and the like, and the protrusions as shown in the figure cause the snapping operation by thicknesses of the left and right side walls. The upper case 35 and lower case 36 forming the storage case are formed of a material capable of causing elastic deformation such as a synthetic resin or the like, and preferably, include an X-ray impermeable additive such as barium sulfate and the like.

Figure 7D:
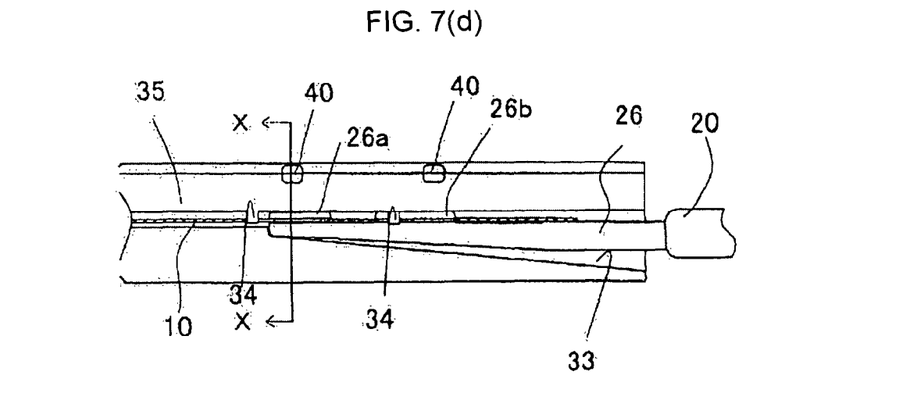

In the upper case 31 with the integrally formed blade fixing piece 34 as described previously, when the attaching finger 26 is inserted in the insertion guide hole 33, the front end of the first engagement portion 26a of the finger pushes the upper case 35 upward against the elastic force of the locking protrusions 40. At this point, the gap is formed between the upper support face 31 and lower support face 32, and the surgical knife blade 10 is supported by the fixing piece 34, and is only movable vertically. In this state, the edge portion of the first fit hole 11 formed in the surgical knife blade is fitted into the slit concave portion 26a of the attaching finger 26. In the state of FIG. 7(d) where the fit is completed, the first engagement portion 26a of the attaching finger 26 pushes the upper case 35 upward by the upper face thereof, the locking edge 35a climbs over the locking protrusions 40, and the upper case 35 separates from the lower case 36. After the separation, the upper case 35 is held by elastic recovery of the locking protrusions 40 while floating on the protrusions 40, and the blade fixing piece 34 of the upper case separates from the fit hole 11 of the surgical knife blade. At the same time, a surgical knife blade pull-out opening is formed between the upper case 35 and lower case 36.

Referring to FIGS. 6 and 7, described next is a method of attaching the surgical knife blade 10 stored in the storage case 30 as described above to the holder 20 configured as described above. First, the above-mentioned attaching finger is fixed to the holder body in the blade attachment position by locking the lock hook member (fixing means) 24 in the first lock groove. Further, the surgical knife blade 10 is fixed and laid by the blade fixing piece (blade fixing means) 34 in the storage case 30. In this state, the holder 20 is in the state of FIG. 6(a), and the attaching finger 26 is fixed and held while protruding outside from the storage barrel 20b. In this state, the first engagement portions 26a and second engagement portions 26b of the attaching finger 26 are fixed in positions to protrude outside.

Figure 6C:
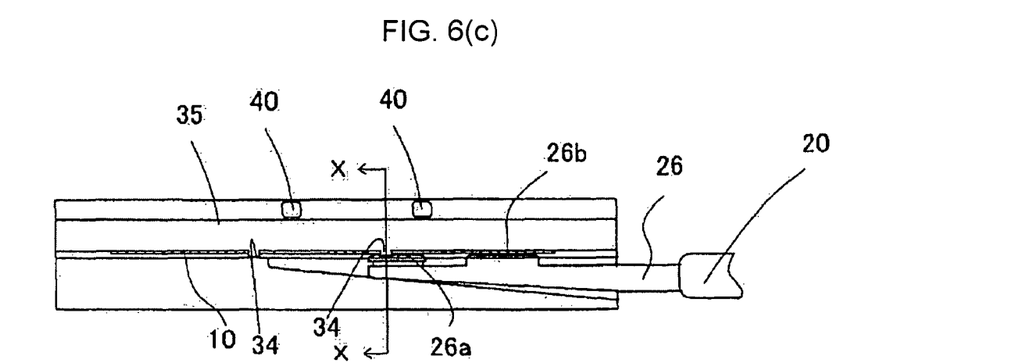
Figure 6D:
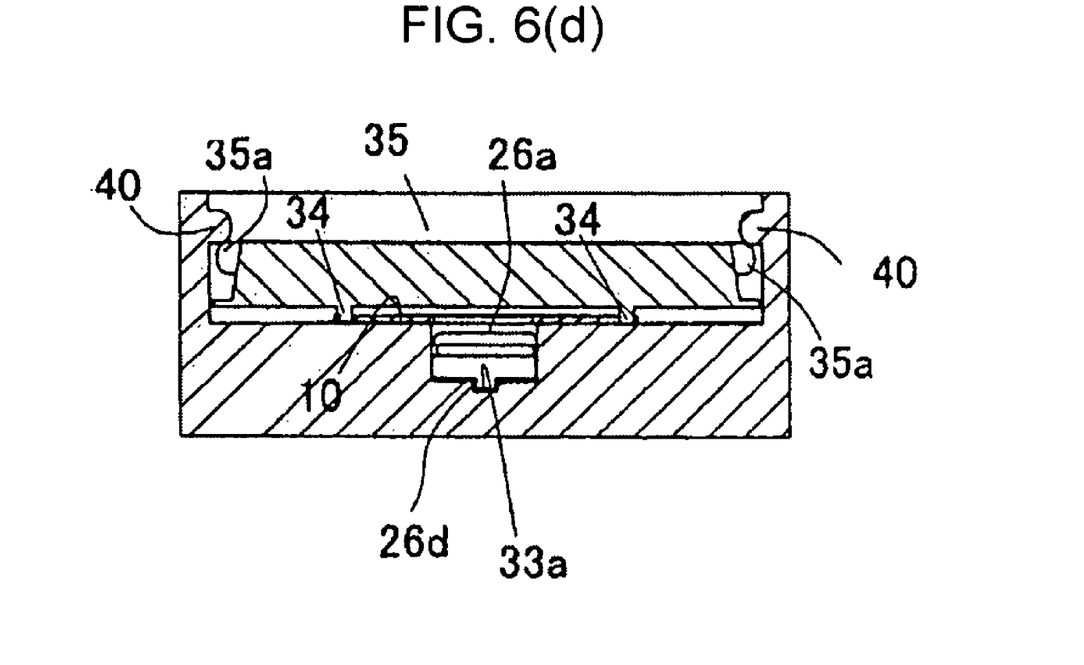
Figure 6E:
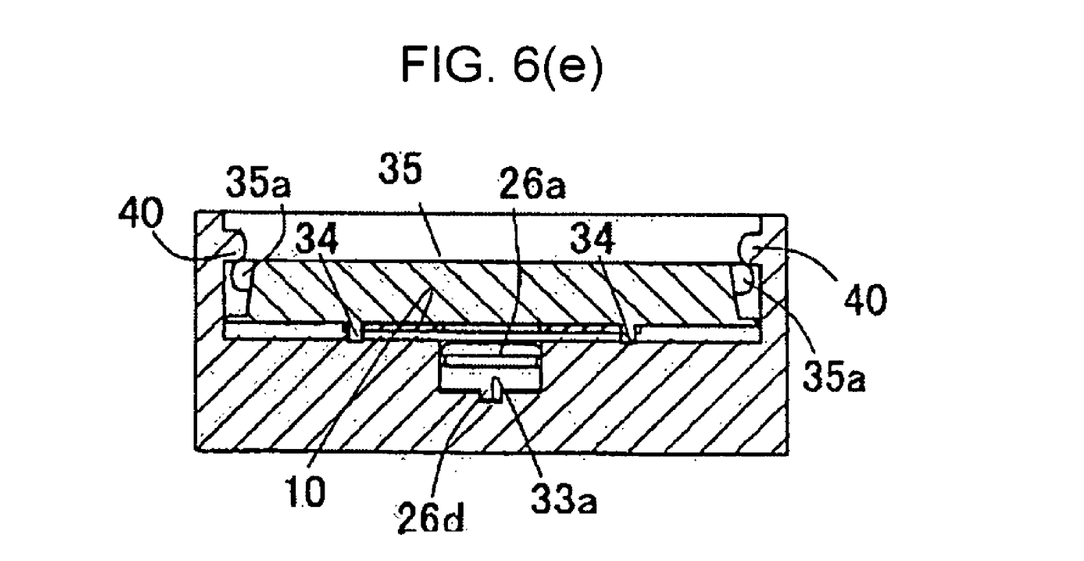

Second, the attaching finger 26 is inserted into the insertion guide hole 33 of the blade storage case, thereby fitting the engagement portion formed in the attaching finger into the fit hole formed in the surgical knife blade, and is attached. FIGS. 6(b), 6(C) and 7(d) show this state. These figures are explained sequentially. In FIG. 6(b), the surgical knife blade 10 is stored in the storage case 30 as shown in FIG. 5, where the blade 10 is sandwiched between the upper support face 31 and lower support face 32 and supported by the blade fixing piece 34. FIG. 6(b) shows an initial state of the attaching finger 26 of the holder 20 being inserted into the insertion guide hole 33. At this point, the guide 26d formed of the protrusion on the attaching finger 26 side engages in the guide rail 33a formed in the insertion guide hole and smoothly enters. In this state, the blade 10 is supported by the blade fixing pieces 34 (two portions in the figure) protruding from the upper support face 31 being fitted into the engagement concave recess portions 14.

Next, FIG. 7(d) shows a state where the attaching finger 26 further travels forward in the insertion guide hole 33 and comes into contact with the lower face of the blade 10. As described previously, since the insertion guide hole 33 is inclined an angle of α as shown in the figure, the first engagement portion 26a located at the front end of the attaching finger 26 comes into contact at its upper face with the lower face of the blade, and pushes the blade upward. At this point, the blade 10 is supported by the engagement concave recess portions 14 engaging in the blade fixing pieces 34, and floats along the pins forming the fixing pieces without moving horizontally. Next, when the attaching finger 26 travels to the position of the attachment fit hole 11 of the blade 10, the first engagement portion 26a at the front end of the attaching finger engages in the first fit hole 11a of the blade 10. This engagement is made by the slit concave portion 26c on the side face of the first engagement portion 26a meshing with the edge portion of the fit hole 11a. The attaching finger 26 further travels forward in this engagement state, and reaches the attachment position of FIG. 7(d), and the first engagement portion 26a on the finger side is fitted into the first fit hole 11a on the blade side, while the second engagement portion 26b is fitted into the second fit hole 11b. Concurrently with the fit, the upper face of the first engagement portion 26a pushes the upper support face 31 upward. A push-up amount is set to cause an engagement state such that the blade fixing piece 34 does not separate from the engagement concave recess portion 14 by the inclined angle of α of the attachment fit hole.

Meanwhile, in the upper case 35 and lower case 36, the locking protrusions 40 and locking edge 35a are fitted with each other as described previously, and in the states of FIGS. 6(b) and 6(c), the upper case is held in the position that the upper support face 31 supports the blade 10. When the upper case 35 is pushed up by the attaching finger 26, as shown in FIG. 7(d), the lower case 36 bends and is deformed. In this state, the blade fixing piece 34 is engaged with the blade 10. In this state, the blade 10 is completely attached to the attaching finger 26, and is fixed to the finger.

Figure 7E:
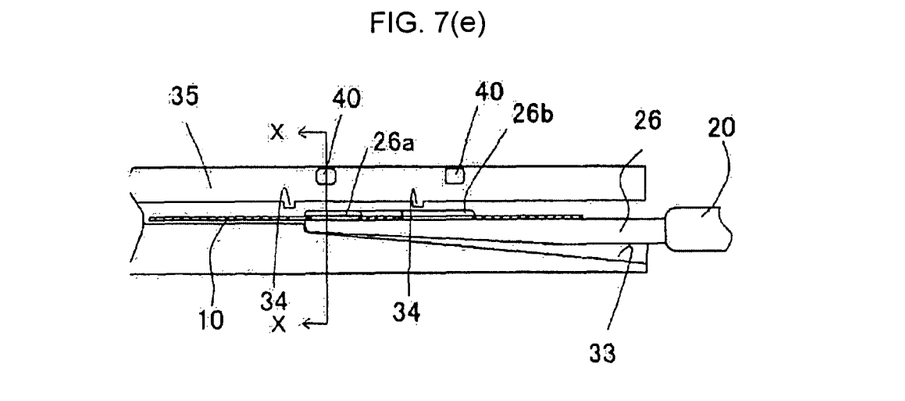

Third, after the surgical knife blade is attached as described above, the blade fixing means (blade fixing piece as shown in FIG. 5) inside the storage case is released, and after the blade fixing means separates from the surgical knife blade, the attaching finger is pulled out of the storage case. This state is shown in FIG. 7(e). When the attaching of the blade is completed, the locking protrusions 40 of the lower case 36 recover to the original state from the state in FIG. 7(d) where the protrusions 40 are elastically deformed after a time delay. By this recovery, the state as shown in FIG. 7(e) is obtained, and the locking protrusions 40 on the lower case 36 side push the locking edge (protrusion) 35a on the upper case 35 side upward. Then, the upper case 35 separates from the lower case 36, and the blade fixing piece 34 formed in the upper support face 31 is removed from the engagement concave recess portion 14 of the blade 10, and releases the engagement. Therefore, when the attaching finger 26 is pulled out of the insertion guide hole 33 by a grasp handle 20, the finger with the blade 10 attached thereto is pulled out of the storage case.

Figure 7F:
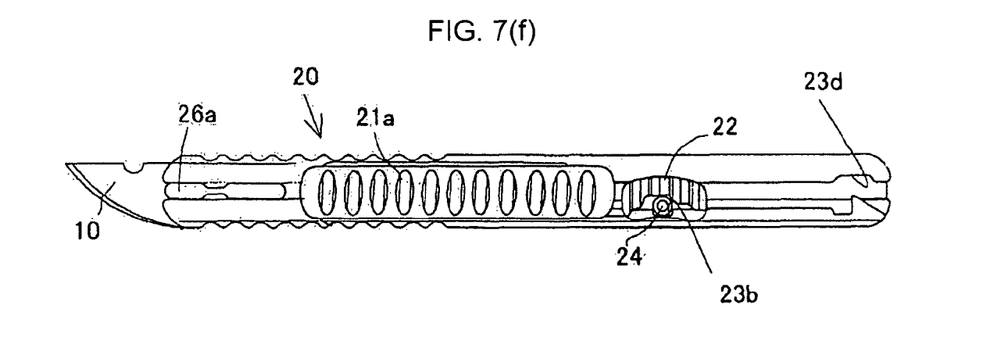
Figure 7G:
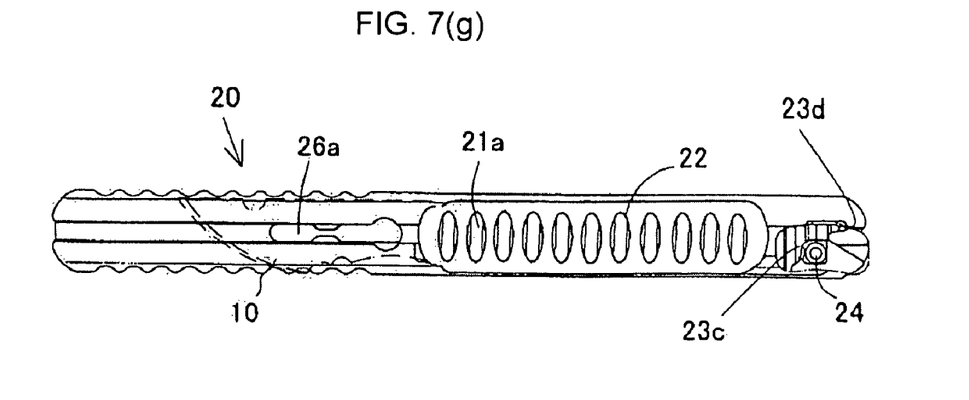
Figure 7H:
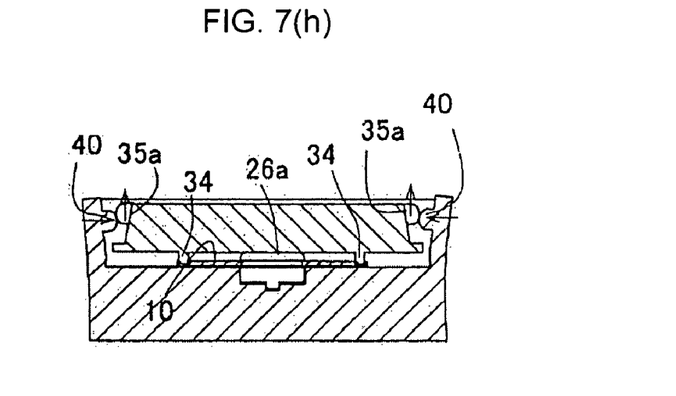
Figure 7I:
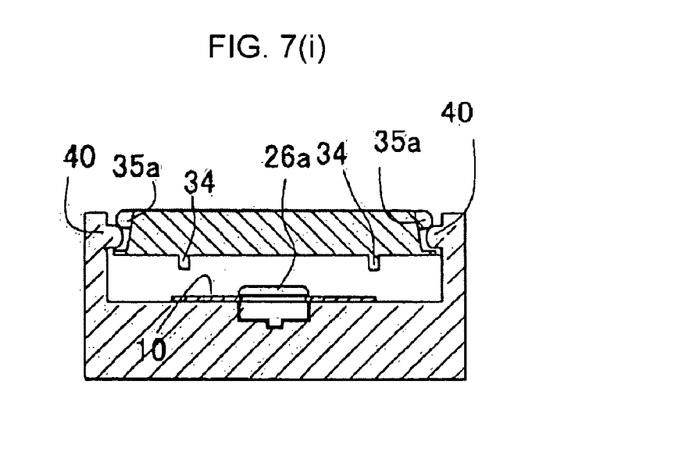

Fourth, the attaching finger is next moved to the blade use position of the holder body, and the blade base portion is fixed by the storage barrel (fixing means) 20b of the holder body. This state is shown in FIG. 7(f). The lock operating piece 22 of the holder 20 is operated to release the lock hook member 24 from the first lock groove 23a, and the slide operating piece 21a is operated to move to the right viewed in the figure. Then, the lock hook portion 24 is locked in the second lock groove 23b. At this point, the surgical knife blade 10 fitted and mounted into the engagement portion of the attaching finger 26 is reliably fixed by the base portion 10a thereof being supported by the side wall of the storage barrel 20b, and in this state, used in medical operations and the like.

Then, after the blade is used, similarly, the lock operating piece is operated to separate the lock hook member 24 from the second lock groove 23b, and the surgical knife blade 10 is stored in the storage barrel 20b using the slide operating piece 21a. Then, the lock hook member 24 is locked in the third lock groove 23c, and this state is maintained.

Figure 8A:
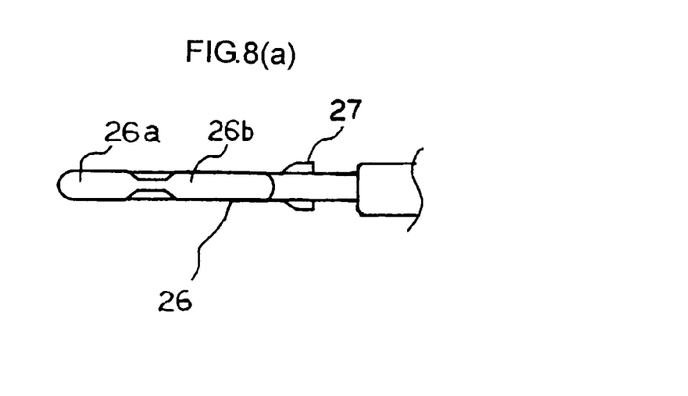
FIG. 8*a* shows a plan view and FIG. 8*b* shows a side view for an example of the slide member of the holder handle 20 to ease separation of an upper case and lower case of the storage case.
Figure 8B:
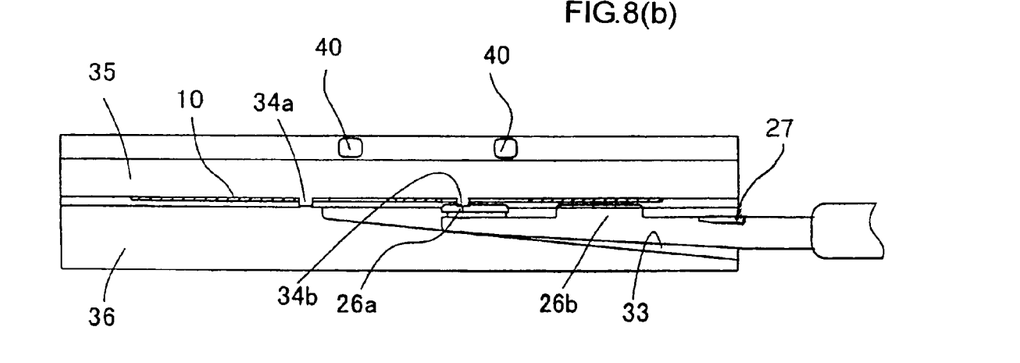

FIG. 8 shows an example of the slide member 21 of the holder handle 20. As shown in FIG. 8(a), a wing member 27 may be provided on the back side of the attaching finger 26 of the holder handle 20 so as to readily separate the upper case 35 and lower case 36 forming the storage case. As shown in FIG. 8(b), in inserting the attaching finger 26 of the holder handle toward the back of the insertion guide hole 33 of the storage case to separate the upper case 35 and lower case 36, the wing member 27 enters the gap between the upper case 35 and lower case 36, and eases separation of the upper case 35 and lower case 36.

INDUSTRIAL APPLICABILITY

The present invention relates to a surgical knife blade holder enabling a surgical knife blade stored in a storage case to be attached to a holder body with a single motion, and has industrial applicability.

The invention claimed is:
1. A holder for a surgical knife blade, comprising:
a holder body that has a blade storage barrel and that is formed in an appropriate shape to grasp;

a slide member that is supported slidably by the blade storage barrel;

an attaching finger that is formed in part of the slide member to attach a surgical knife blade;

a slide operating piece that is integrally formed with the slide member;

a lock hook member that prevents the slide member from sliding;

locking concave grooves that are disposed in a slide guide edge of the holder body which guides the slide member slidably and that engage in the lock hook member; and lever means, coupled to the slide member, for supporting the lock hook member while biasing the lock hook member toward the locking concave grooves, wherein the locking concave grooves are formed in an attachment position where the surgical knife blade is attached to the attaching finger in the slide member, in a use position where the attached blade is fixed, and in a storage position where the surgical knife blade is stored in the storage barrel;

wherein the attaching finger is provided with an engagement portion adapting to a fit hole formed in the surgical knife blade, and in an edge of the engagement portion is formed a wing to support a drop of the surgical knife blade when the surgical knife blade is fitted, and wherein in the attaching finger, in its upper plane is formed an engagement portion which is fitted into the surgical knife blade, and in its rear bottom is formed an insertion guide which adapts to an insertion guide of a storage case storing the surgical knife blade and guides insertion of the attaching finger.

2. The holder for the surgical knife blade according to claim 1, wherein the insertion guide adapts to a protrusion or a concave-shaped groove that is the insertion guide of the storage case.

3. The holder for the surgical knife blade according to claim 1, wherein the slide member is provided with a wing member, at the back of the attaching finger corresponding to the attachment position where the surgical knife blade is attached to the attaching finger of the slide member, to separate an upper case and a lower case forming a storage case.

4. The holder for the surgical knife blade according to claim 3, wherein the wing member is formed so that a thickness at its front end portion is thinner than a thickness at its rear end portion.

* * * * *